US00PP21216P2

(12) United States Plant Patent
Hartman

(10) Patent No.: US PP21,216 P2
(45) Date of Patent: Aug. 17, 2010

(54) ***CALADIUM* PLANT NAMED 'WHITE DELIGHT'**

(50) Latin Name: *Caladium×hortulanum*
Varietal Denomination: White Delight

(76) Inventor: Robert Dale Hartman, 158 Blue Moon Ave., Lake Placid, FL (US) 33852

( * ) Notice: Subject to any disclaimer, the term of this patent is extended or adjusted under 35 U.S.C. 154(b) by 42 days.

(21) Appl. No.: 12/321,742

(22) Filed: Jan. 23, 2009

(51) Int. Cl.
*A01H 5/00* (2006.01)

(52) U.S. Cl. ..... Plt./373

(58) Field of Classification Search ..... Plt./373, Plt./263.1
See application file for complete search history.

*Primary Examiner*—Kent L Bell
(74) *Attorney, Agent, or Firm*—C. A. Whealy

(57) ABSTRACT

A new and distinct cultivar of *Caladium* plant named 'White Delight', characterized by its intermediate plant habit; vigorous and dense growth habit; rapid growth rate; and strap-type leaves that are white to grey-green in color with white-colored main veins and dark green-colored borders.

3 Drawing Sheets

Botanical designation: *Caladium×hortulanum.*
Cultivar denomination: 'WHITE DELIGHT'.

BACKGROUND OF THE INVENTION

The present invention relates to a new and distinct cultivar of *Caladium* plant, botanically known as *Caladium×hortulanum*, commercially referred to as a strap leaf-type *Caladium* and hereinafter referred to by the name 'White Delight'.

The objective of the Inventor's breeding program is to create new *Caladium* cultivars that have uniform plant habit, exceptional performance and attractive foliage coloration.

The new *Caladium* plant originated from a cross-pollination made by the Inventor in April, 2001, in Lake Placid, Fla. of *Caladium×hortulanum* 'White Wing', not patented, as the female, or seed, parent with *Caladium×hortulanum* 'Jackie Suthers', not patented, as the male, or pollen, parent. The new *Caladium* plant was discovered and selected by the Inventor as a single plant within the progeny of the stated cross-pollination in a controlled outdoor nursery environment in Lake Placid, Fla. on Jun. 15, 2002.

Asexual reproduction of the new *Caladium* plant by tuber divisions in a controlled outdoor nursery environment in Lake Placid, Fla. since Apr. 15, 2003 has shown that the unique features of this new *Caladium* plant are stable and reproduced true to type in successive generations of asexual reproduction.

SUMMARY OF THE INVENTION

Plants of the new *Caladium* have not been observed under all possible environmental conditions. The phenotype may vary somewhat with variations in environment such as temperature and light intensity, without, however, any variance in genotype.

The following traits have been repeatedly observed and are determined to be the unique characteristics of 'White Delight'. These characteristics in combination distinguish 'White Delight' as a new and distinct cultivar of *Caladium:*

1. Intermediate plant habit.
2. Vigorous and dense growth habit; rapid growth rate.
3. Strap-type leaves that are white to grey-green in color with white-colored main veins and dark green-colored borders.

Plants of the new *Caladium* differ from plants of the female parent, 'White Wing', in the following characteristics:

1. Plants of the new *Caladium* are more compact than plants of 'White Wing'.
2. Plants of the new *Caladium* grow faster than plants of 'White Wing'.
3. Leaves of plants of the new *Caladium* are more rounded than and not as pointed as leaves of plants of 'White Wing'.
4. Plants of the new *Caladium* and 'White Wing' differ in leaf coloration as plants of 'White Wing' have white-colored leaves with a broader and mottled dark and light green-colored borders.

Plants of the new *Caladium* differ from plants of the male parent, 'Jackie Suthers', in the following characteristics:

1. Plants of the new *Caladium* are more compact than plants of 'Jackie Suthers'.
2. Plants of the new *Caladium* grow slower than plants of 'Jackie Suthers'.
3. Plants of the new *Caladium* and 'Jackie Suthers' differ in leaf coloration as plants of 'Jackie Suthers' have white-colored leaves blushed with pink and broad green-colored borders.

Plants of the new *Caladium* can be compared to plants of 'Florida White Ruffles', disclosed in U.S. Plant Pat. No. 14,402. In side-by-side comparisons conducted in Lake Placid, Fla., plants of the new *Caladium* differed primarily from plants of 'Florida White Ruffles' in the following characteristics:

1. Plants of the new *Caladium* were more upright than plants of 'Florida White Ruffles'.
2. Leaves of plants of the new *Caladium* were more rounded than and not as pointed as leaves of plants of 'Florida White Ruffles'.
3. Plants of the new *Caladium* and 'Florida White Ruffles' differed in leaf coloration as plants of 'Florida White Ruffles' had creamy white-colored leaves with dark green-colored borders.

Plants of the new *Caladium* can also be compared to plants of 'Candidum Junior', not patented. In side-by-side comparisons conducted in Lake Placid, Fla., plants of the new *Caladium* differed primarily from plants of 'Candidum Junior' in the following characteristics:

1. Plants of the new *Caladium* were more compact and denser than plants of 'Candidum Junior'.

2. Plants of the new *Caladium* had strap-type leaves whereas plants of 'Candidum Junior' had fancy-type leaves.

BRIEF DESCRIPTION OF THE PHOTOGRAPHS

The accompanying photographs illustrate the overall appearance of the new *Caladium*. These photographs show the colors as true as it is reasonably possible to obtain in colored reproductions of this type. Colors in the photographs may differ slightly from the color values cited in the detailed botanical description which accurately describe the colors of the new *Caladium*.

The photograph on the first sheet is a side perspective view of a typical plant of 'White Delight' grown in a container in a shadehouse.

The photograph at the top of the second sheet is a side perspective view of typical plants of 'White Delight' (top center), 'Florida White Ruffles' (left) and 'Candidum Junior' (right) grown in a shadehouse.

The photograph at the bottom of the second sheet is a side perspective view of typical plants of 'White Delight' (top center), 'Jackie Suthers' (left) and 'White Wing' (right) grown in a shadehouse.

The photograph at the top left of the third sheet is a top perspective view of typical plants of 'White Delight' grown in an outdoor nursery.

The photograph at the top right of the third sheet is a close-up view of a typical inflorescence of 'White Delight'.

The photograph at the bottom of the third sheet is a close-up view of typical freshly-dug tubers and roots of 'White Delight'.

DETAILED BOTANICAL DESCRIPTION

The aforementioned photographs and following observations and measurements describe plants grown in 15-cm containers in Avon Park, Fla. during the spring in a polypropylene-covered shadehouse and plants grown in ground beds in Zolfo Springs, Fla. during the late summer in an outdoor nursery. All plants were grown under conditions and practices which approximate those generally used in commercial *Caladium* production. During the production of the plants, day temperatures ranged from about 29° C. to 35° C., night temperatures ranged from about 22° C. to 26° C. and light levels were about 8,000 foot-candles (shadehouse) or 10,000 to 12,000 foot-candles (outdoor nursery). Plants had been growing in the shadehouse for nine weeks from planting tubers when the photographs and the detailed description were taken. Plants had been growing in the outdoor nursery for seven months from planting tuber pieces when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'White Delight'.

Parentage:

*Female, or seed, parent.*—*Caladium×hortulanum* 'White Wing', not patented.

*Male, or pollen, parent.*—*Caladium×hortulanum* 'Jackie Suthers', not patented.

Propagation:

*Type.*—By tubers and by tuber divisions.

*Time to initiate roots, summer.*—About seven to ten days at 32° C.

*Time to initiate roots, winter.*—About two to three weeks at 24° C.

*Tuber description* (*outdoor nursery-grown plants*).—Appearance: Multi-segmented; individual segments ovate to rounded in shape. Height: About 3.5 cm. Diameter: About 5.2 cm. Texture: Thick, starchy; somewhat brittle. Color: Epidermis, close to 164D to lighter than 200D, with development, close to 200A to 200B; interior, between 2D and 10D. Root description: Dense, thick, fleshy; white, close to 155C, in color.

Plan description:

*Plant type.*—Herbaceous perennial.

*Plant/growth habit.*—Upright and intermediate plant habit; inverted triangle; rapid growth rate; vigorous, dense growth habit; suitable for 15-cm to 25-cm containers. Leaf petioles arising from tubers; petioles mostly upright and leaning outwardly with development.

*Plant height, from soil level to top of leaf plane, shadehouse-grown plants.*—About 21 cm to 23 cm.

*Plant height, from soil level to top of inflorescences, shadehouse-grown plants.*—About 29 cm.

*Plant diameter or spread, shadehouse-grown plants.*—About 38 cm to 42 cm.

*Cataphylls* (*only observed on shadehouse-grown plants*).—Length: About 4.3 cm to 10 cm. Width: About 1.5 cm. Shape: Lanceolate. Apex: Acute. Base: Sheathing the stem. Color, inner and outer surfaces: Close to 199B to 199C with fine streaks, close to 147A; distal margin may be tinged with close to N170D; with development, color becoming closer to 200A.

Foliage description:

*Length, shadehouse-grown plants.*—About 12 cm to 18 cm.

*Width, shadehouse-grown plants* (*flattened*).—About 8.5 cm to 14.7 cm.

*Shape.*—Ovate.

*Apex.*—Acuminate to acute.

*Base.*—Sagittate to cordate.

*Margin.*—Entire; undulate.

*Texture, upper surface.*—Smooth, glabrous.

*Texture, lower surface.*—Smooth, glabrous; glaucous.

*Venation pattern.*—Pinnate.

*Color, shadehouse-grown plants.*—Developing leaves, upper surface: Center: Close to 155C to 155D; towards the borders, sectors of close to 191B to 191C or close to 191B with flecking/streaking of close to 146A; basal notch, close to 187C. Border and margins: Close to 147A. Venation: Midrib, close to N155D; lateral veins, close to 156D. Developing leaves, lower surface: Center: Close to 155C; basal notch, close to 187C. Border and margins: Close to 147B. Venation: Midrib, close to 155D; lateral veins, close to 160D. Fully expanded leaves, upper surface: Center: Close to 155B; towards the borders, sectors of close to 194B to 194C or close to 194B with flecking/streaking of close to 146A to 146B; basal notch, close to 187C. Border and margins: Between 147A and 146A. Venation: Midrib, close to 155B; lateral veins, close to 155C. Fully expanded leaves, lower surface: Center: Close to 155A; basal notch, close to 187C.

Border and margins: Close to 147A to 147B. Venation: Midrib, between 155A to 150D; lateral veins, close to 160D.

*Petiole.*—Aspect: Mostly erect, leaning outwardly with development. Length, shadehouse-grown plants: About 14 to 19 cm. Diameter, distal, shadehouse-grown plants: About 3 mm to 3.5 mm. Diameter, proximal, shadehouse-grown plants: About 5 mm to 9 mm. Color, proximal, shadehouse-grown plants: Close to 199B to 199C tinged with close to 148A to 148B with fine streaks and speckles of close to 147A. Color, distal, shadehouse-grown plants: Close to N155C. Wing length, shadehouse-grown plants: About 3.5 cm to 6.5 cm. Wing diameter, shadehouse-grown plants: About 9 mm to 12 mm. Wing color, shadehouse-grown plants: Close to 199B to 199C with fine streaks and speckles of close to 147A.

Inflorescence description: Inflorescences only observed on shadehouse-grown plants.

*Inflorescence arrangement.*—Upright hooded spathes surrounding a columnar spadix borne on a tall upright scape. Spadix with sessile, simple female and male flowers separated into two zones. Female flowers arranged on the lower one-third of the spadix; male flowers arranged on the upper two-thirds of the spadix. Sterile flowers develop between female and male flower zones; near this area, the spathe constricts surrounding the female flowers.

*Fragrance.*—None detected.

*Natural flowering season/longevity.*—Plants of the new *Caladium* typically flower during the spring or early summer in central Florida. Flowers develop about nine weeks after growth commences. Inflorescences last about three days before fading; inflorescences persistent.

*Spathe.*—Length: About 11.5 cm. Width, distal: About 4.4 cm. Width, proximal: About 2.5 cm. Width, at constriction: About 1.5 cm. Shape: Ovate to somewhat obovate. Apex: Acute to acuminate. Base: Tapering. Margin: Entire; slightly reflexed. Texture, upper and lower surfaces: Smooth, glabrous. Color: Front surface: Upper two-thirds: Close to 158C; color becoming closer to 199C to 199D with development. Lower one-third: Close to 147C to 147D tinged with close to 187B; color becoming closer to 146B to 146C with development. Rear surface: Upper two-thirds: Close to 160C to 160D tinged and streaked with close to 147C and 146C, variably streaked with close to 181B to 181C. Lower one-third: Close to 146B to 146C. Spadix: Length, entire spadix: About 8.4 cm. Length, male flower zone: About 6.6 cm. Length, sterile flower zone: About 9 mm. Length, female flower zone: About 1.8 cm. Diameter, male flower zone: About 9.5 mm. Diameter, sterile flower zone: About 7 mm. Diameter, female flower zone: About 1 cm. Shape: Spindle-shaped to columnar. Apex: Acute. Base: Obtuse. Aspect: Upright. Color, mature, male zone: Close to 158C to 158D. Color, mature, sterile zone: Close to 158C to 158D. Color, mature, female zone: Close to 179D. Male flowers: Quantity per spadix: About 192. Shape: Obovate. Height: About 3 mm. Diameter: About 3 mm. Anther color: Close to 158C to 158D. Amount of pollen: Sparse. Pollen color: Close to 11C. Female flowers: Quantity per spadix: About 156. Shape: Obovate. Height: About 3 mm. Diameter: About 2 mm. Stigma color: Close to 9D. Ovary color: Close to 155C to 155D. Scape: Length: About 17.5 cm. Diameter: About 7 mm. Strength: Sturdy; flexible. Aspect: Erect. Texture: Smooth, glabrous; glaucous. Color: Proximal: Close to 148A to 148B with fine streaks and speckles, darker than 147A. Distal: Close to 146A to 146B.

*Seed and fruit.*—Seed and fruit development have not been observed on plants of the new *Caladium.*

Disease/pest resistance: Plants of the new *Caladium* have been observed to be somewhat tolerant to *Pythium* root rot and *Xanthomonas* leaf spot. Plants of the new *Caladium* have not been observed to be resistant to pests or other pathogens common to *Caladium.*

Temperature tolerance: Plants of the new *Caladium* have been observed to be tolerant to temperatures ranging from about 7° C. to about 40° C.

It is claimed:

1. A new and distinct *Caladium* plant named 'White Delight' as illustrated and described.

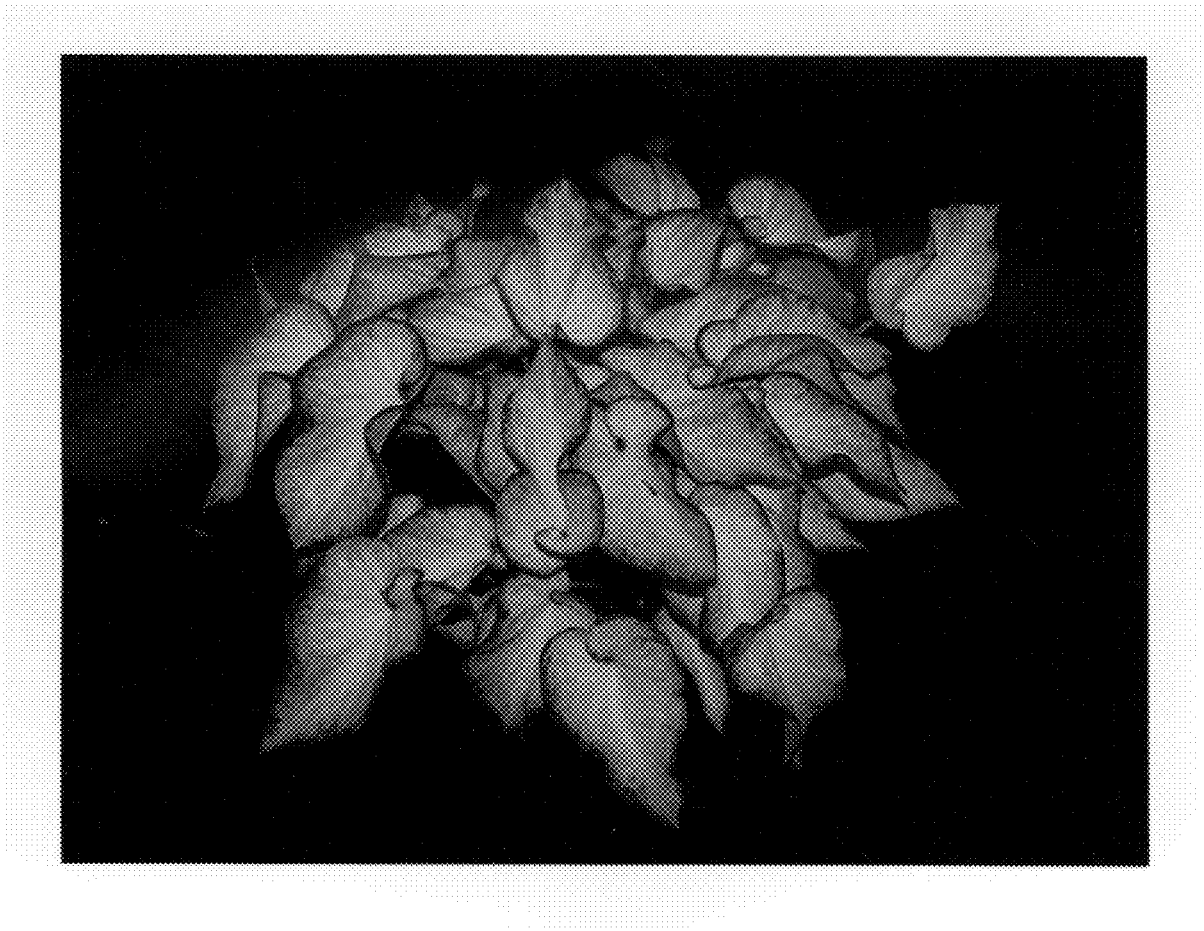

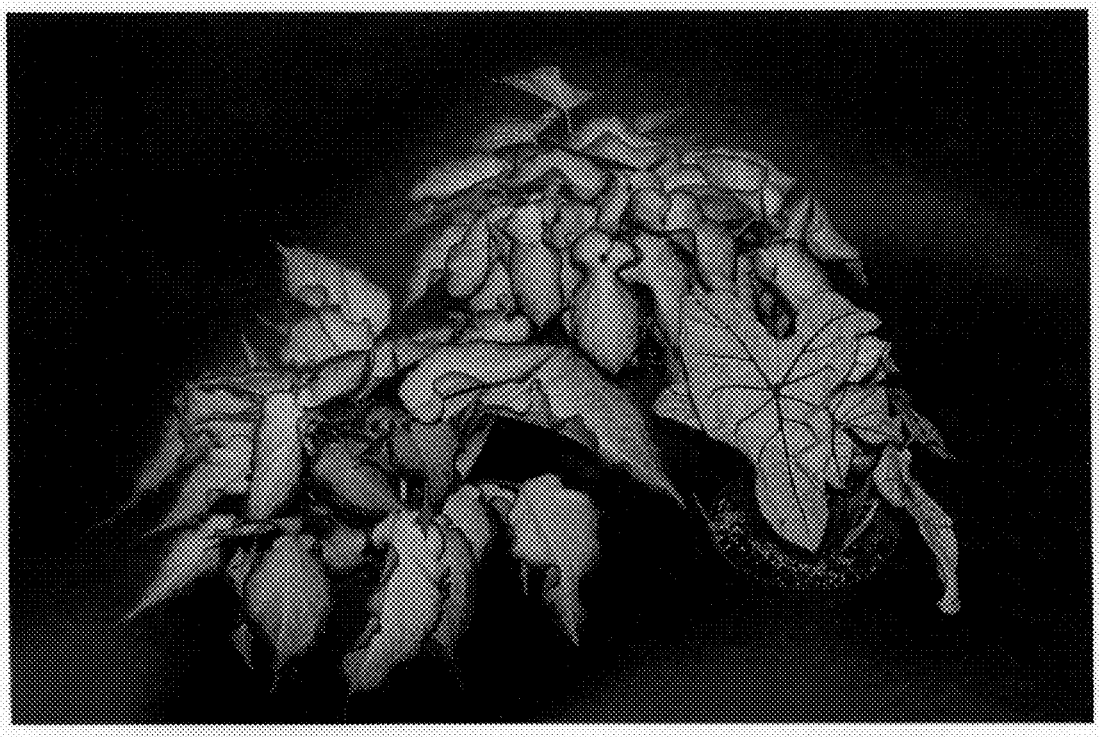
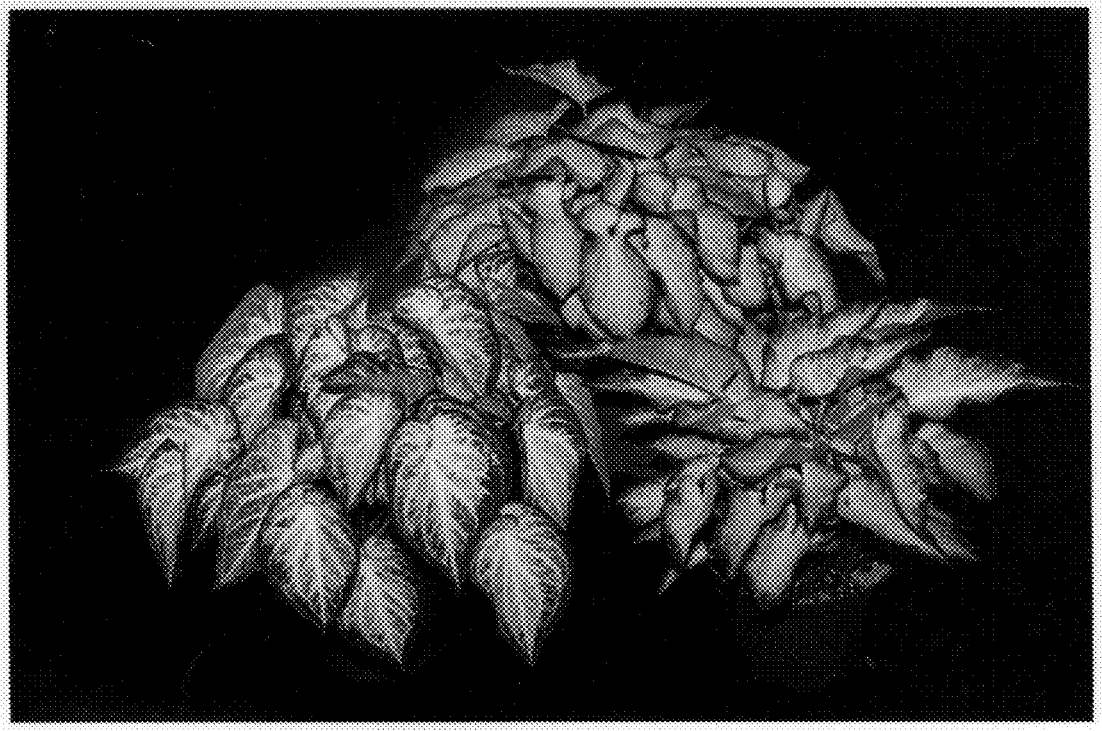

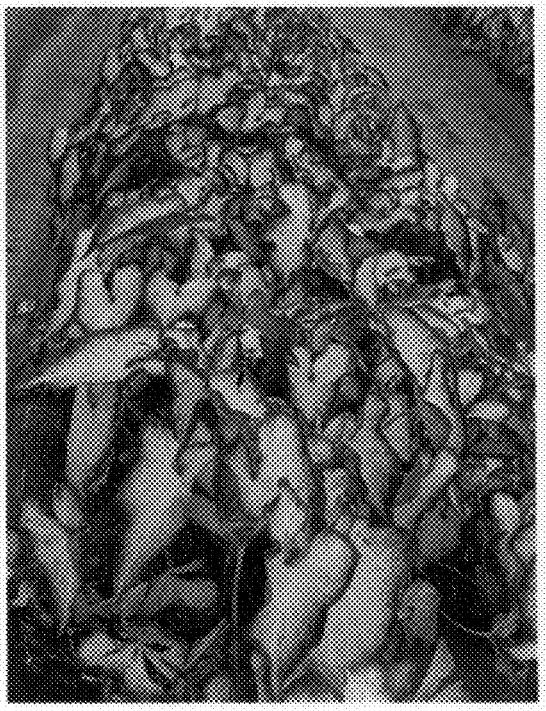
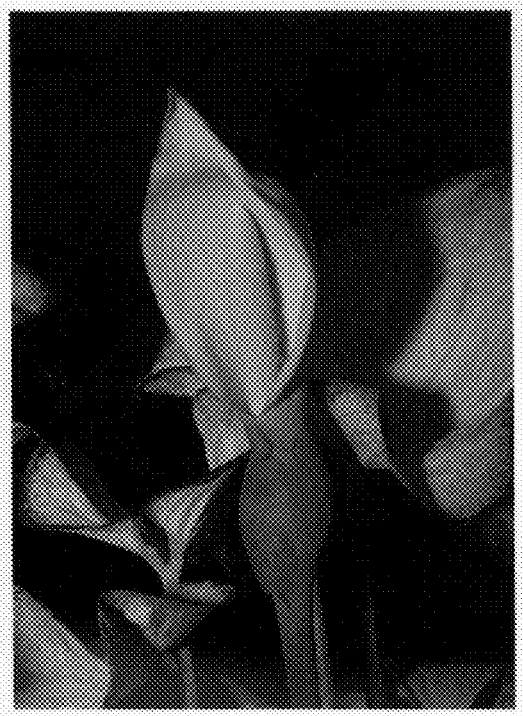
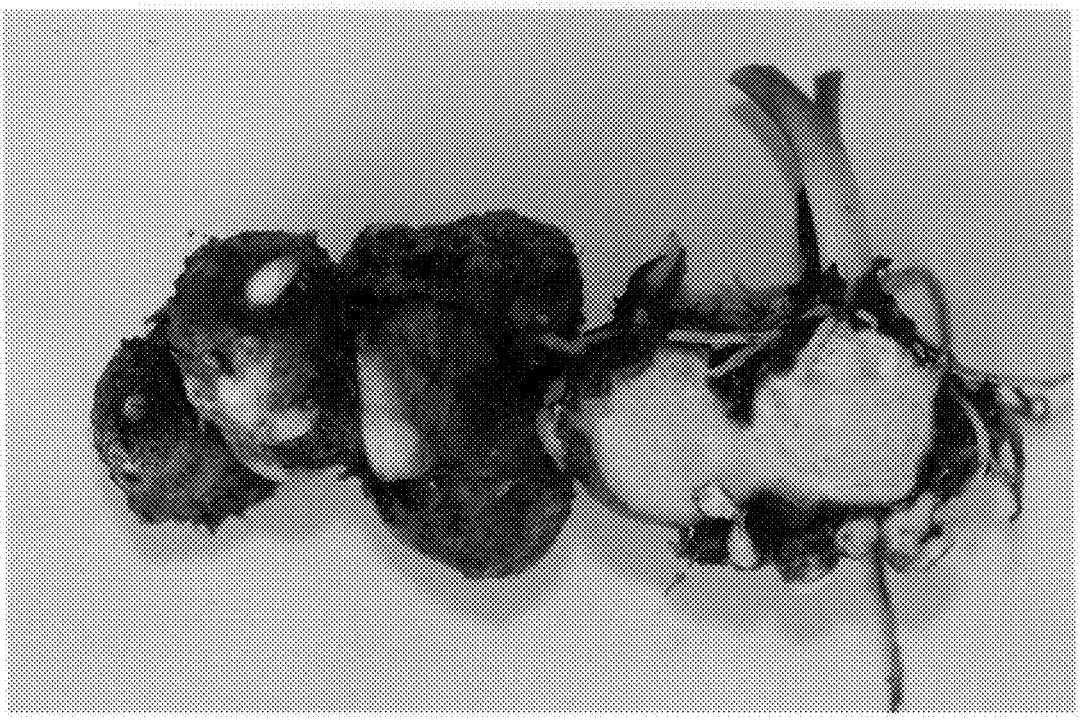

* * * * *